United States Patent
Nelson et al.

(10) Patent No.: US 11,961,149 B2
(45) Date of Patent: *Apr. 16, 2024

(54) SYSTEMS AND METHODS FOR MONITORING MOVEMENT OF DISEASE

(71) Applicant: BE SEEN BE SAFE LTD., Guelph (CA)

(72) Inventors: Timothy Nelson, Haliburton (CA); Joel Roberto Sotomayor, Aurora (CA)

(73) Assignee: FARM HEALTH GUARDIAN LTD., Guelph (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,700

(22) Filed: Jan. 9, 2023

(65) Prior Publication Data

US 2023/0230179 A1 Jul. 20, 2023

Related U.S. Application Data

(63) Continuation of application No. 16/241,281, filed on Jan. 7, 2019, now Pat. No. 11,593,896, which is a
(Continued)

(51) Int. Cl.
*H04W 4/02* (2018.01)
*A01K 11/00* (2006.01)
(Continued)

(52) U.S. Cl.
CPC ............ *G06Q 50/02* (2013.01); *A01K 11/008* (2013.01); *G06F 16/23* (2019.01); *G06F 16/248* (2019.01);
(Continued)

(58) Field of Classification Search
CPC ....... G06Q 50/02; G16H 50/80; H04W 4/029; H04W 4/30; H04W 4/021; G06F 16/23;
(Continued)

(56) References Cited

U.S. PATENT DOCUMENTS

| | | | | |
|---|---|---|---|---|
| 2005/0261841 A1* | 11/2005 | Shepard | ................ | G16H 50/80 702/32 |
| 2006/0282295 A1* | 12/2006 | McComb | ............... | G06Q 50/02 705/4 |

(Continued)

*Primary Examiner* — Dai Phuong
(74) *Attorney, Agent, or Firm* — Bennett Jones LLP; Salvatore F. Barbieri; Lorelei G. Graham

(57) ABSTRACT

A method for monitoring disease across agricultural areas of interest is provided comprising displaying at least one virtual zone corresponding to an agricultural geographic area of interest on a map in an application on a first device, and receiving an alert message when the first device is in proximity to a virtual zone. The at least one virtual zone is defined by at least one geofence. Each virtual zone is associated with a level of risk that indicates a likelihood of an outbreak of a disease detrimental to agriculture. Each virtual zone is configured to receive access notification information from each geofence when tracked devices enter an area defined by that geofence. The access information includes the level of risk associated with other virtual zones from which the tracked devices came. The alert message indicates if the first device should enter that virtual zone.

21 Claims, 13 Drawing Sheets

Related U.S. Application Data continuation of application No. 14/905,550, filed as application No. PCT/CA2014/000571 on Jul. 17, 2014, now Pat. No. 10,188,048.

(60) Provisional application No. 61/847,247, filed on Jul. 17, 2013.

(51) Int. Cl.
| | |
|---|---|
| *G06F 16/23* | (2019.01) |
| *G06F 16/248* | (2019.01) |
| *G06F 16/29* | (2019.01) |
| *G06Q 50/02* | (2012.01) |
| *G16H 50/80* | (2018.01) |
| *H04L 67/12* | (2022.01) |
| *H04W 4/021* | (2018.01) |
| *H04W 4/029* | (2018.01) |
| *H04W 4/30* | (2018.01) |

(52) U.S. Cl.
CPC ............ *G06F 16/29* (2019.01); *G16H 50/80* (2018.01); *H04L 67/12* (2013.01); *H04W 4/021* (2013.01); *H04W 4/029* (2018.02); *H04W 4/30* (2018.02)

(58) Field of Classification Search
CPC ..... G06F 16/248; G06F 16/29; A01K 11/008; H04L 67/12
See application file for complete search history.

(56) References Cited

U.S. PATENT DOCUMENTS

| | | | |
|---|---|---|---|
| 2009/0312660 A1* | 12/2009 | Guarino | G16H 50/80 600/529 |
| 2013/0030931 A1* | 1/2013 | Moshfeghi | H04W 4/027 705/16 |
| 2013/0154795 A1* | 6/2013 | Devaux | G07C 9/22 340/5.65 |
| 2013/0222141 A1* | 8/2013 | Rhee | G16H 50/80 340/573.3 |
| 2016/0016171 A1* | 1/2016 | Goel | G01N 33/48707 435/7.1 |

* cited by examiner

| Date | Visitor Name | Time in | Time out |
|---|---|---|---|
| 10-Jan-13 | Masterfeeds Truck No. 416 | 9:45 | 10:15 |
| 10-Jan-13 | Burnbrae Egg Pick Up Truck ID – BB7671 | 10:12 | 11:04 |
| 10-Jan-13 | Mike Jones Veterinarian Stratford Veterinary Clinic | 15:17 | 18:42 |

Be Seen Be Safe Visitor Record

Maxwell

Date Range — From 10-Jan-13 — To 10-Jan-13

Visitor selection — All Visitors

Report date — 16-May-13

Figure 11

SYSTEMS AND METHODS FOR MONITORING MOVEMENT OF DISEASE

CROSS REFERENCE TO RELATED APPLICATIONS

This application is a continuation of U.S. patent application Ser. No. 16/241,281 filed on Jan. 7, 2019, which is a continuation of U.S. patent application Ser. No. 14/905,550 filed on Jan. 15, 2016, which is a national stage entry of PCT/CA2014/000571 filed Jul. 17, 2014, and claims the benefit of U.S. Provisional Patent Application No. 61/847,247 filed Jul. 17, 2013, all of which are herein incorporated by reference in their entirety.

FIELD

The embodiments described herein relate to systems and methods for monitoring movement of disease, and in particular, to systems and methods for monitoring movement of disease between agricultural zones.

INTRODUCTION

In the event of an infectious disease outbreak in plant or animal agriculture, the ability to track and trace where a disease originated and to project where it may have moved to, and consequently may next 'break', may facilitate mitigation of its spread. There exists potential for disease causing organisms to be transported from one location to another on animals, humans, plant material, organic matter, equipment and vehicles over long periods of time and great distances.

These disease transport agencies may be referred to as disease vectors (e.g., living things, animals, birds, insects, plants, plant materials, and the like) and fomites (e.g. any inanimate object via which pathogenic organisms may be transferred, which may not support growth).

Records of visits to at risk properties may be held at each individual property location. These records may be kept in a manual form in a visitor log book. Compliance (filling in the details required) may be poor, especially by regular visitors such as staff and regular farm service personnel such as livestock feed delivery trucks. In the event of a disease outbreak the log book for the individual affected property may serve as a historical record of who has been on that property and when they were there and for what purpose. It may not however assist in ascertaining where they were before they visited the property nor where they went once they had left the property. Thus there is limited data to assist in ascertaining where the disease may have originated. The limited data may also not enable or assist with forward projection of where the disease organism may have moved on to, carried by the visitor(s).

There exists a need for real-time monitoring and analysis of the movement of disease, vectors, and/or fomites, on, off, and between at risk properties with a view to mitigating the impact of a disease outbreak, or at least a useful alternative.

BRIEF DESCRIPTION OF DRAWINGS

Various embodiments will now be described, by way of example only, with reference to the following drawings, in which:

FIG. 8 is a schematic diagram of a user interface providing a report for a user according to some embodiments;

FIG. 10 is a schematic diagram of a user interface providing a report for a user according to some embodiments;

FIG. 11 is a schematic diagram of a user interface providing another mapping report according to some embodiments;

DESCRIPTION OF VARIOUS EMBODIMENTS

Figure 1:
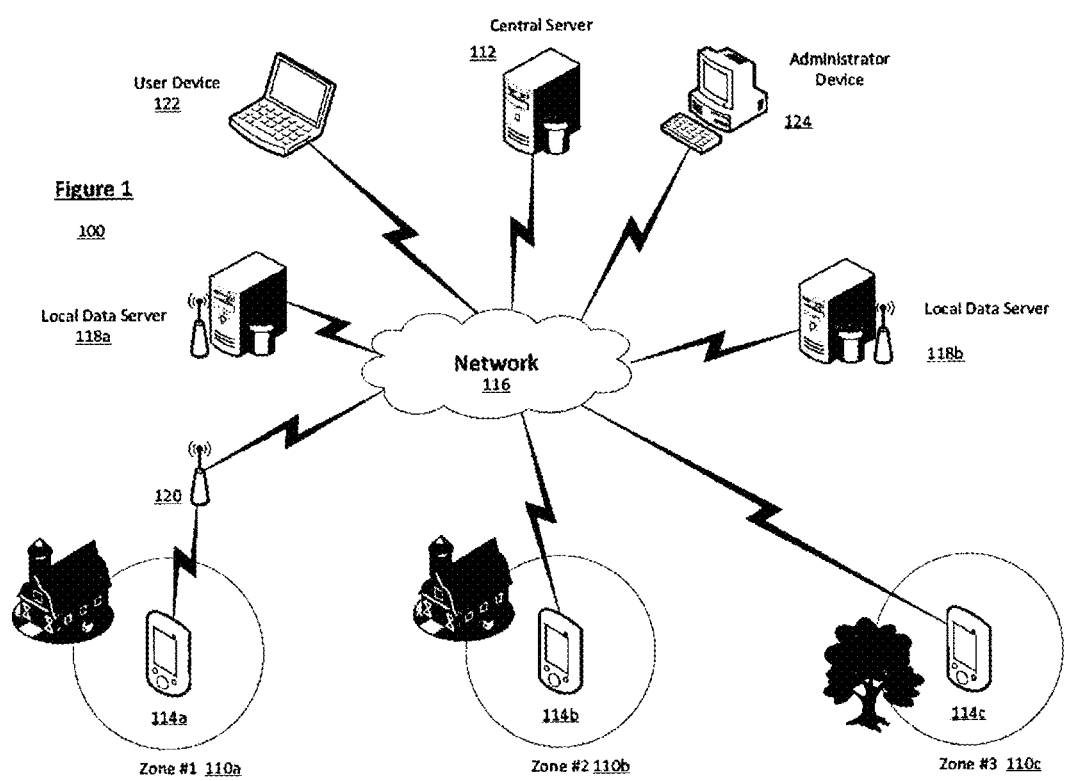
FIG. 1 is a schematic diagram of a system for monitoring movement of disease according to some embodiments.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, personal data assistant, cellular telephone, smartphone device, UMPC tablets and wireless hypermedia device or any other computing device capable of being configured to carry out the methods described herein.

Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for inter-process communication (IPC). In still other embodiments, there may be a combination of communication interfaces implemented as hardware, software, and combination thereof.

Each program may be implemented in a high level procedural or object oriented programming or scripting language, or both, to communicate with a computer system. However, alternatively the programs may be implemented in assembly or machine language, if desired. The language may be a compiled or interpreted language. Each such computer program may be stored on a storage media or a device (e.g., ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, non-transitory computer readable medium that bears computer usable instructions for one or more processors. The medium may be provided in various forms, including one or more diskettes, compact disks, tapes, chips, magnetic and electronic storage media, volatile memory, non-volatile memory and the like. Non-transitory computer-readable media may include all computer-readable media, with the exception being a transitory, propagating signal. The term non-transitory is not intended to exclude computer readable media such as primary memory, volatile memory, RAM and so on, where the data stored thereon may only be temporarily stored. The computer useable instructions may also be in various forms, including compiled and non-compiled code.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein.

Referring now to FIG. 1, there is shown a monitoring system 100 for monitoring movement of a disease according to some embodiments. The monitoring system 100 is operable to use geofencing methodology to provide a discreet and accurate mechanism to monitor and record the movement of disease vectors (animals, insects carried by an animal, etc.) or fomites (inanimate objects, machinery, vehicles etc.), on and off, or between predefined geographic regions (e.g. agricultural geographic areas of interest).

In the event of a disease outbreak the data collected and processed by monitoring system 100 may be used to generate and provide vector and fomite movement data and mapping of the potential movement from an origin to current region(s) of spread of a disease and possibly infected and/or infectious plants or animals. System 100 may provide forward and backward disease projections as reports.

System 100 defines virtual zones 110, where each virtual zone corresponds to an agricultural geographic area of interest. The virtual zones may be defined by a geofence. Geofencing is a technology that defines a virtual boundary around a real world geographical area. In doing so, a radius of interest is remotely established that can trigger a response in a tracking device 114 (e.g. GPS device, SPS device, RFID device, location determination device, computing device) that has been programmed to respond as it crosses the virtual boundary. Event detection (e.g. tracking device 114 entering or exiting a zone, disease outbreak, suspected disease outbreak) can in turn can trigger other predefined operations by system 100. Geofencing allows automated responses to be initiated based on the defined coordinates of a geographic area and the predefined response programmed into the system 100 for that geographic area.

Geofencing may use global positioning system (GPS), satellite positioning systems (SPSs), or radio frequency identification (RFID) (as non-limiting examples) to define geographical boundaries around properties or regions of interest. A geofence is a virtual barrier. Monitoring system 100 is operable to dynamically generate a geofence or virtual zone, i.e. by defining a radius around properties or points of interest. Monitoring system 100 is operable to define a geo-fence as a predefined set of boundaries.

The virtual zones may correspond to different types of agricultural properties or geographic areas of interest. These types may be stored by system 100 in a zone record, along with other data about the zone. For example, "hot properties" may be properties or areas where the presence of an infectious agent is confirmed. As another example, "at risk properties" may be livestock operations, crop production operations, packing facilities, processing locations, abattoirs, or other locations where livestock, crops, or vectors and fomites which travel between these locations may be concentrated. These may be areas of interest that are at risk to diseases detrimental to agriculture and where people working in the area of interest may also be at risk of contracting zoonotic diseases commonly associated with livestock and poultry. A non limiting example may be certain strains of Avian Influenza H5N1. As a further example, "primary control zones" may be geographic areas which are designated by the appropriate regulatory authority to be restricted or with no access because of the possibility of disease spread. These are non-limiting examples only and system 100 may classify additional types of agricultural geographic areas of interest.

Monitoring system 100 may include one or more central servers 112 which may be implemented using a computer system having one or more processors and one or more data storage devices configured to communicate with tracking devices 114 configured with tracking applications. The central server 112 may be coupled to tracking devices 114 via network 116.

Monitoring system 100 may also include one or more local servers 118 operable to collect data from tracking devices 114 for provision to central server 112 in a tiered manner. The local servers 118 may be in closer proximity to tracking devices 114 than the central server 112 facilitating data collection and transmission. Local servers 118 may be distributed within a geographic area and feed data to a central server 112 for the area.

In some embodiments, there may be transceiver devices 120 that may collect data from tracking devices 114 for provision to local servers 118 or central server 112 in a tiered manner. The transceiver devices 120 may be closer in proximity to the tracking devices 114 than the central server 112 and local servers 118 facilitating data collection and transmission. For example, the tracking devices 114 may have more limited data transmission and receiver hardware than the transceiver devices 120 and local servers 118, for example. Accordingly, transceiver devices 120 and local servers 118 may provide a data relay mechanism between tracking devices 114 and central server 112. There may be multiple central servers 112, transceiver devices 120 and local servers 118 distributed over geographic areas in various configurations.

One or more user devices 122 may be coupled to local servers 118 or central server 112 via network 116. User device 122 may be used to create an account accessed using authentication information (username, passcode). User device 122 may be associated with different types of users. Account data may be stored as a user account record at central server 112, for example. User devices 122 may provide report parameters and queries and receive reports from central server 112, or local server 118. User devices 122 may provide alert configuration parameters receive alerts from central server 112, or local server 118.

For example, user device 122 may be associated with owners, farmers, companies, or managers or agricultural geographic area of interests defined by virtual zones 110. For each of the virtual zones 110, user device 122 may provide registration data particular to a property owner or manager for the virtual zone 110. The registration data may be stored as part of the user account record. A user account may also be associated with one or more virtual zones 110 (e.g. an owner may own or a manager may manage multiple zones 110). There may also be a separate account record for each zone 110. Each zone 110 may be classified by a type of zone, such as a hot zone, at risk property, primary control zone, and the like.

User device 122 may be used to access a user interface to provide report and alert parameters, and receive report information and alerts particular to their related zones 114. Example user interface reports and displays are provided herein. The user account may be updated with data updates for the zones 110. For example, a zone may change type over a period of time, such as changing from an at risk property to a hot zone, for example. As another example, each zone may be associated with a level of risk, that may vary over a period of time.

Each zone 110 may be associated with a unique zone identifier, which may be stored as part of the zone 110 account record or user account record. As will be explained herein, data related to the zone 110 may include the unique identifier thereby enabling system 100 to identify related data. For example, disease outbreak data may be linked with a location generally (used by system 100 to correlate to the geographic location of the zone 110) or with a specific zone identifier for one or more zones 110. The disease outbreak data may report the outbreak of a disease at a location or zone 110.

System 100 is operable to dynamically update account records for zones 110. For example, system 100 may associate a level of risk to each zone 110 which provides an indication of a likelihood of outbreak of a disease detrimental to agriculture within the corresponding agricultural geographic area of interest. There may also be a disease outbreak field indicating current disease outbreaks, or past disease outbreaks. Visits by tracking devices 114 to the zone may be stored as part of the zone 110 or user account record. The tracking device 114 visit information will be updated and linked to the zone 110, either as part of a zone record (e.g. dynamic and automated visitor log), or linked thereto via the zone identifier. Disease outbreaks may also be stored as part of the zone 110 or user account record. These fields may change over time.

As another example, user device 122 may be associated with a user of tracking devices 114 (e.g. truck operator, livestock owner, supply company). User device 122 may provide registration data particular to a tracking device 114. For example, each tracking device 114 may be associated with vector or fomite that has the potential to carry the disease detrimental to agriculture, and a descriptor for the vector or fomite may be stored in the tracking device 114 account record. The descriptor may describe the type of vector or fomite being tracked by tracking device 114, for example. The registration data may be particular to the vector or fomite and link the vector or fomite to associated tracking device. Each tracking device 114 may be associated with a unique device identifier, which may be stored as part of the tracking device 114 account record. Data received from tracking device 114 may include the unique identifier thereby enabling system 100 to identify which tracking device 114 the data was received from. For example, location related data may be received from tracking devices 114 to track movement of the vector or fomite associated therewith within and between zones 110.

Other illustrative and non-limiting example user types include veterinarians, public health workers, sellers of agricultural products, industry associated, government regulators, and so on.

Users may have limited access to data stored by system 100. User device 122 may be restricted access to data and may only access their own records, or a limited scope of records. For example, a company can see employee records. A public health official may receive summaries of abstracted data for example, or data which other users consent access to. Accordingly each record may be associated with an access level to facilitate determination of scope of data access. User's may also be associated with access levels, which may change dynamically.

System 100 may also include an administrative device 124 for use by an administrator of system 100 (e.g. a super user) that may have access to all records or data, groups of user records, or a large subset of records and data maintained by system 100. An administrator may configure central server 112, for example, via administrator device 124, and may update rules and modules, data, etc.

A tracking device 114 may be configured with a tracking application that may interact with a central server 112, local servers 118, or transceiver devices 120. The tracking application may be configured to identify a virtual boundary/geofenced area around a zone 110 (e.g. agricultural facility or predefined area of interest to agriculture) or provide location details to determine whether the tracking device 114 is within a zone 110. The tracking application may implement GPS, SPS, RFID, or other location determination technology. The central server 112 collects data relating to tracking devices 114 with tracking applications entering and exiting geo-fenced zones 110.

Figure 2:
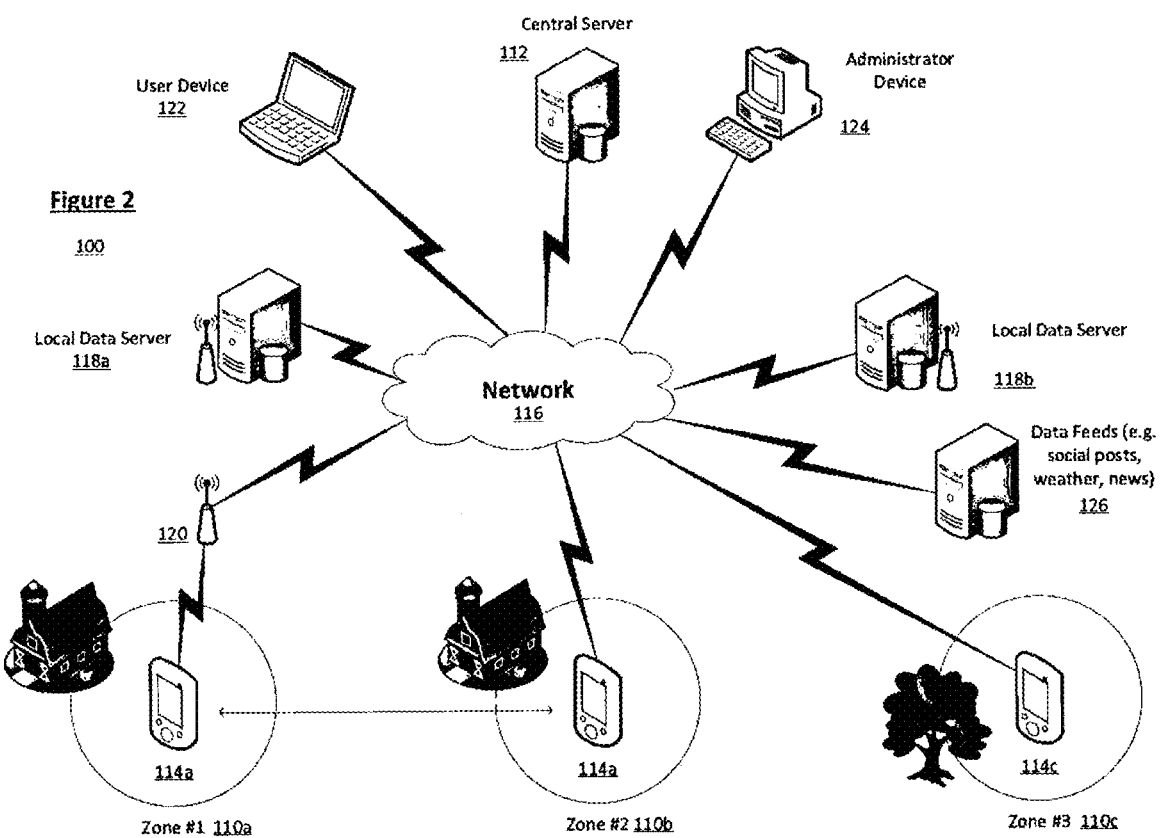
FIG. 2 is a schematic diagram of another system for monitoring movement of disease according to some embodiments.

Referring now to FIG. 2 there is shown another example schematic of a monitoring system 100 according to some embodiments.

Central server 112 may receive data from a variety of data feeds 126 (e.g. servers with processors and data storage devices configured to receive and transmit real-time data). Data received via data feeds 126 may be stored as data records for correlation against other records (e.g. tracking device records, user records, zone records, disease records, etc.)

System 100 integrates and processes any form of real-time data streams 126 to enhance the user's understanding of seemingly unrelated events and put them together to form a new view of an event. For example, data feeds 126 may relate to data from social media postings, new events, mapping data, geographic data, historical data, topography data, disease outbreak alerts, suspected disease outbreak alerts (and updates thereto, e.g., confirming that a disease was or was not present after testing), meteorological data, weather patterns (e.g. prevailing winds may increase transmission of disease), travel routes of possible vectors and fomites of disease (e.g. veterinarian, feed company vehicles, livestock transport vehicles), factual information about diseases (e.g. incubation, transmission, historical outbreaks, treatments).

System 100 is operable to aggregate the data from data feeds 126 together with other data collected by system 100 to form a highly weaved and rich meta-data view of outbreak or disease related events. System 100 may link disease events (e.g. disease spotted on farm) with non-obvious suspects (e.g. a feed company source of supply has been contaminated, prevailing winds) which may lead to new ways of processing and analyzing large seemingly unconnected datasets. System 100 is operable to move beyond surface data points directly focused on disease and integrate other data feeds 126 (with no limit of the type of data streams) in real time to get a holistic view. The end results is that system 100 may create a super-rich data-set made up of various obvious disease related data-sets and nonrelated data-sets.

FIG. 2 further illustrates movement of a tracking device 114a between zones 110a, 110b. Tracking devices 114 may visit one or more zones 110. A zone 110 may also receive visits by one or more tracking devices 114.

Figure 4:
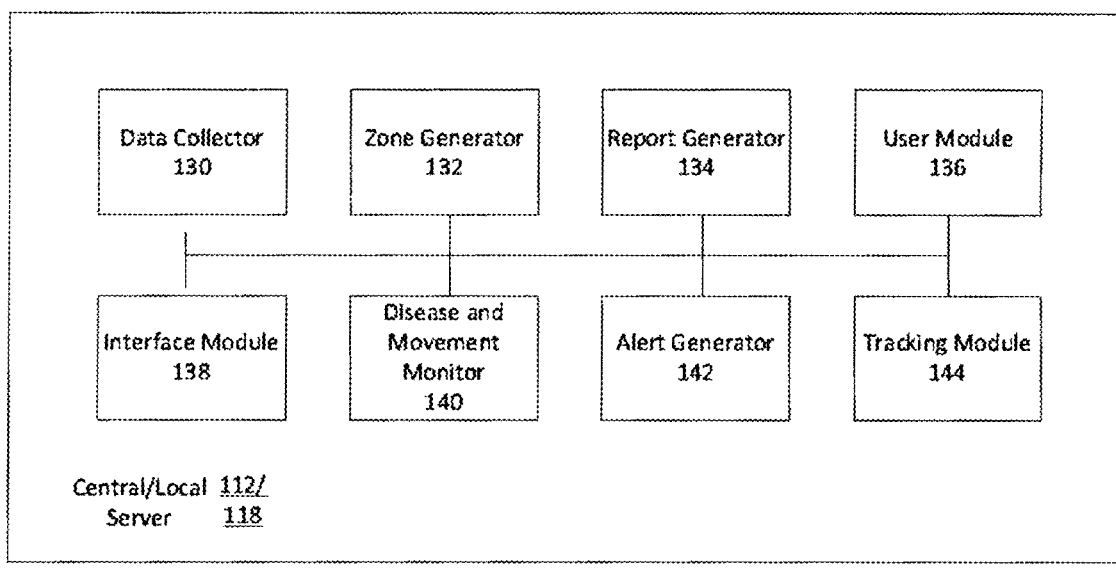
FIG. 4 is a schematic diagram of central or local server according to some embodiments.

Referring now to FIG. 4 there is shown a schematic diagram of central server 112 (or local server 118) according to some embodiments. Central server 112 or local server 118 may be configured for monitoring movement of disease across agricultural areas of interest.

Central server 112 (or local server 118) may be implemented using a server and data storage devices configured with database(s) or file system(s), or using multiple servers or groups of servers distributed over a wide geographic area and connected via a network 116. Central server 112 may be connected to a data storage device directly or to a cloud based data storage device via network 116. Central server 112 may reside on any networked computing device including a processor and memory, such as a personal computer, workstation, server, portable computer, mobile device, personal digital assistant, laptop, tablet, smart phone, WAP phone, and portable electronic devices or a combination of these.

Central server 112 may include one or more microprocessors that may be any type of processor, such as, for example, any type of general-purpose microprocessor or microcontroller, a digital signal processing (DSP) processor, an integrated circuit, a programmable read-only memory (PROM), or any combination thereof. Central server 112 may include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like.

Central server 112 may include one or more input devices, such as a keyboard, mouse, camera, touch screen and a microphone, and may also include one or more output devices such as a display screen and a speaker. Central server 112 has a network interface in order to communicate with other components, to serve an application and other applications, and perform other computing applications by connecting to network 116 (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. Although only one central server 112 is shown for clarity, there may be multiple central servers 112 or groups of central servers 112 distributed over a wide geographic area and connected via e.g. network 116.

Central server 112 includes a processor and a storage device storing instructions, the instructions being executable to configure the processor to provide a number of functional elements including: a data collector 130, a zone generator 132, a report generate 134, a user module 136, an interface module 138, a disease movement monitor 140, an alert generator 142, and a tracking module 144. A service or communication bus enables asynchronous communication and data exchange between the central server 112 components. The modules may be distributed over central server 112 and local server 118, or there may be corresponding one or more modules on each, depending on the functionality of central server 112 and local server 118. Some central servers 112 and local servers 118 may have different modules than others.

Figure 6:
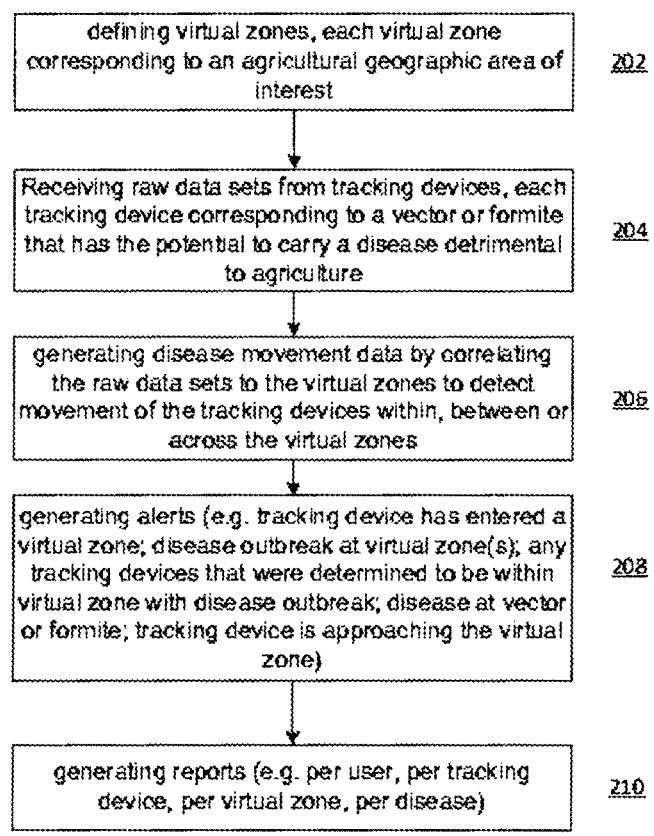
FIG. 6 is a flow chart diagram of a method for monitoring movement of disease according to some embodiments.

FIG. 6 is a flow chart diagram of a method 200 for monitoring movement of disease according to some embodiments, and will be referred to along with FIG. 4 to illustrate operations of the components of central server 112. One or more steps of method 200 may be repeated or occur simultaneously by different components, and there may be various orders of operation.

At 202, zone generator 132 is operable to define virtual zones 110 (e.g. geofences), where each virtual zone 110 corresponds to an agricultural geographic area of interest. As described herein, each virtual zone 110 may also be associated with a user (e.g. property owner, farmer, manager, company account) and a unique identifier. A virtual zone 110 may be defined by a set of geographic coordinates corresponding to a agricultural geographic area of interest. A virtual zone 110 may be defined by a point of interest and a radius, as another example. A virtual zone 110 may be referred to herein as a geofence. A virtual zone may be dynamically defined, such as in response to a report disease outbreak. A virtual zone 110 may be defined by processing mapping applications to detect agricultural areas of interest. A virtual zone 110 may be defined by a user via user device 122 by submitting geographic information for the zone 110. These are examples only and zones 110 may be defined by a variety of mechanisms.

At 204, a data collector 130 is operable for receiving and preprocessing raw data sets from tracking devices 114. The data collector 130 may preprocess raw data by removing extraneous data sets, reformatting data, reorganizing or reordering the data, segmenting the data into sub data sets, normalizing the data, converting the data into different metrics, and so on.

Each raw data set includes an identification code identifying the corresponding tracking device 114 the raw data was received from. A raw data set may also include a timestamp corresponding to the time the raw data was generated by the tracking device 114, and location information for the corresponding tracking device 114. The raw data may also be from raw data feeds 126, as described herein. For example, the raw data may relate to weather data, social posts, geographical data, topographical data (e.g. prevailing winds), disease spread trends, historical disease data, factual data about disease (incubation, transmission mode), real-time disease data on suspect disease outbreaks, disease outbreaks, and updates on suspects (e.g. confirmed not to be an outbreak, wrong diagnosis), news, and so on. The raw data may indicate the outbreak of a disease at a virtual zone 110 or location. The raw data may also indicate an outbreak of a disease in associated with a vector or fomite corresponding to a tracking device 114. The raw data may also relate to properties about zones 110, or vectors or fomites, such as levels of risk, and the like.

Figure 5:
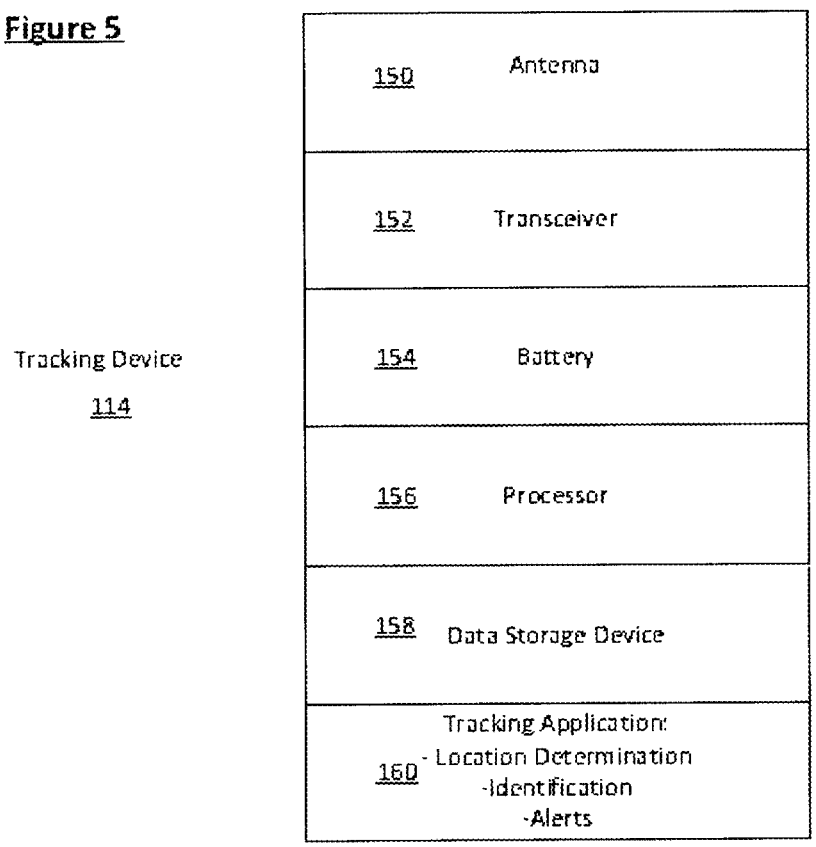
FIG. 5 is a schematic diagram of a tracking device according to some embodiments.

Referring now to FIG. 5, there is shown a schematic diagram of a tracking device 114 according to some embodiments.

Each tracking device 114 may correspond to a vector or fomite that has the potential to carry a disease detrimental to agriculture.

Tracking device 114 may include an antenna 150 for transmitting and receiving electronic signals. Tracking device 114 may include a transceiver for receiving commands, data, alerts, and transmitting location based data to transceiver device 120, or directly to central server 112, or local servers 118. Tracking device 114 may include a battery 154 to power the hardware components.

In some example embodiments, a tracking device 114 may be implemented using one or more processors 156 and one or more data storage devices 158 configured with database(s) or file system(s), or using multiple servers or groups of servers distributed over a wide geographic area and connected via a network (which may be referred to as cloud computing). Tracking device 114 may reside on any networked computing device, such as a personal computer, workstation, server, portable computer, GPS device, SPS device, RFID device, location determination device, mobile device, personal digital assistant, laptop, tablet, smart phone, WAP phone, and portable electronic devices or a combination of these.

Processor 156 may be any type of processor, such as, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Data storage device 158 may include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Tracking device 114 may include one or more input devices, such as a keyboard, mouse, camera, touch screen and a microphone, and may also include one or more output devices such as a display screen and a speaker. Tracking device 114 has a network interface in order to communicate with other components and perform other computing operations by connecting to network 116 (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. Tracking device 114 may have a simpler configuration such as an RFID, SPS, or GPS tag 128 as will be described herein in relation to FIG. 7.

Tracking device 114 is configured with tracking application 160 which is configured to determine the location of the tracking device 114 (e.g. using GPS, SPS, RFID technology for example). Tracking application 160 is also operable to manage a unique identifier for the tracking device 114 (stored e.g. in storage device 158) for provision with data transmission to assist the receiving component to identify the origin of data. Tracking application 160 is further configured to receive alerts from central server 112 as will be described herein.

Central server 112 defines a set of virtual boundaries. When tracking device 114 crosses a zone 110 this may trigger an action. The virtual boundary may be set to encompass the geographical boundary of an agricultural facility or predefined area of interest to agriculture (geophysical entity) for the purpose of tracking movement potential disease vectors and/or fomites across the virtual boundary using the tracking device 114.

At 206, disease movement monitor 140 is operable to generate disease movement data by correlating the raw data sets to the virtual zones 110 to detect movement of the tracking devices 114 within, between or across the virtual zones 110. Disease movement monitor 140 may also generate movement data using data received from data feeds 126, suspect disease outbreak data, or disease outbreak data, for example. Disease movement data may be dynamically generated in real-time using a variety of mechanisms as new data is received by disease movement monitor 140, data collector 130, or other components of system.

System 100 may comprise two types of servers. Local servers 118 may gather raw data from the tracking devices 114. A central server 112 (or a plurality thereof) may draw data from the local servers 118 into a central storage device with a database. The central server 112 may pool data based on user information (property owner, tracking device user, etc.), identifiers, locations, etc. Further data analysis may be performed by central server 112.

Accordingly, one or more local servers 118 may be configured for receiving the raw data sets and transmitting the raw data sets to the data collector 130 at one or more central servers 112 for processing by the disease movement monitor 140.

Disease movement monitor 140 may match collected data with user information to transform the data from coded information to useable/searchable data related to movement of vectors and/or fomites (e.g. tracking device users) and disease risk across agricultural areas and properties (e.g. zones 110). The data provides information on movement of vectors and/or fomites (via tracking devices 114) across or between geofences based on the tracked movement of a tracker device carried by each vector or fomite.

The tracking device 114 may be a geo-enabled mobile telephone or other portable electronic triggering device which is capable of receiving signals relating to zones 110 as the tracking device 114 passes through the virtual zone 110.

The virtual zone 110 may defined by a geofencing technology. Geofencing allows automatic alerts to be generated based on the defined virtual boundary. A geofence (geolocation) is set around one or more target properties (e.g. geofence zone). This may done remotely using mapping and geolocation application configured by local servers, central servers, or another server (e.g. zone generator 132). A central administrator device 124 or user device 122 may use the mapping and geofencing application to define geofences around properties.

A geofence may be implemented by establishing a virtual perimeter of a geographic area for use with a location-based service, so that if a tracked device 114 enters or exits such an area a notification (e.g. alert) may be generated. Such notification may include information about the location of the geofence-based device 114 that is transmitted to a central server 112, and an alert may be transmitted to user device 122, a mobile telephone or an email account, or directly back to the device 114, for example. A geofence may be used while tracking a geofence-based device being carried by vector or fomite, may evaluate whether such a tracked device is inside or outside a geofence.

Zone generator 132 may establish a geofence by obtaining coordinates of a region of interest and then assuming a boundary of a standard size and shape associated with the region of interest. Zone generator 132 may also establish a geofence based at least in part, upon assumptions regarding dimensions of such particular regions of interest. Alternatively, a geofence may be established manually by allowing a user to "draw" a geofence on a map. Another approach to establishing a geofence includes a process whereby a user edits to improve a geofence created by an application. Zone generator 132 may dynamically generate zones 110 based on received disease outbreak data, suspect disease outbreak data, or other types of data.

Utilizing geofencing, the system 100 provides a virtual boundary around at risk properties, farms and or properties where disease can potentially spread to or from (e.g. zones 110).

When a vector or fomite carrying an electronic triggering device 114 crosses the geofence the event is recorded on a local server 118 or at a central server 112. Other actions generated from within the server may also be triggered by the event depending on how the device 114 is programmed and what instructions have been pre-programmed into the server 112/118.

The central server 112 contains a database to draw the coded information collected through the local server 118. Accordingly, local server 118 may perform preprocessing and coding of raw data (e.g. data collector 130).

In the event of a disease outbreak on a property (e.g. zone 110) the system 110 may assist with the mitigation of disease spread by plotting the course of disease spread by retrieving the information about the movements of all of the disease vectors and/or fomites pre and post visiting a hot property (e.g. zone 110). This information enables backtracking to the potential source of the disease and forward tracking to predict the spread to at risk properties and regions of interest (a region heavily populated with susceptible livestock for example). Where warnings can be issued data on the potential spread of the disease can be displayed as lists or provided as alerts, right down to individual properties or on a map showing a region into which the disease might have spread.

In the event of a disease outbreak on a property (e.g. zone 110) the system 110 may deliver alerts or warnings by automatically selecting specific target audiences who may be at high risk of entering a hot or potentially hot property or area (for example veterinarians), and broadcast emergency warnings to them via user devices 122 (electronic media, SMS, Text, email etc.)

Tracking module 144 is configured to register a tracking device 114 by receiving registration data particular to the corresponding vector or fomite that has the potential to carry the disease detrimental to agriculture. The registration may also involve associating the tracking device 114 with a unique identifier, as described herein, and one or more user identifiers (e.g. users or companies associated with the vectors or fomites).

Each vector or fomite may be assigned a level of risk. Those vectors and fomites that come in contact with livestock and poultry or manure or blood or raw products from livestock and poultry operations being classified as having the highest risk, those vectors and fomites that enter the property or region of interest but who are kept isolated from potential contamination by any of the above constituting the lowest risk. This risk priority may be further enhanced in the system 100 by the use of commonly accepted designated regions (see CFIA Biosecurity Protocols for various livestock and plant sectors) within an at risk property such as Restricted Access Zone (RAZ) highest level of contamination risk to Controlled Access Zone (CAZ) constituting the lowest level of risk. Accordingly, tracking module 144 may assign a level of risk to each vector or fomite and store the level of risk in the device 114 record. The level of risk provides an indication of a likelihood of carrying the disease detrimental to agriculture.

User module 136 is operable to associate a user (e.g. a property owner, manager, farmer, company) with each virtual zone 110. User module 136 may also assign a level of risk to each virtual zone 110, where the level of risk provides an indication of a likelihood of outbreak of a disease detrimental to agriculture within the corresponding agricultural geographic area of interest. The virtual zone 110 may be stored in the zone record or user record. As described herein, each zone 110 may also be associated with a unique identifier for use by system 100 in associating data related to the zone 110 with the zone 110.

At 208, an alert generator 142 is operable for generating an alert regarding a virtual zone upon determining that a tracking device has entered the virtual zone.

The alerts may relate to a variety of disease related information or warnings. For example, the alert may indicate possible disease outbreaks based on received outbreak information and generated movement data. The alert may indicate that a tracking device 114 should not enter into a zone 110 due to risk of disease either based on the vector or fomite associated therewith or the zone 110. The alert may provide an update to data, such as confirming that a disease was not present at past visited zones 110 over a certain time period. Other types of alerts may be used.

For example, in some embodiments central server 112 (or local server 118) may receive real-time disease data, where the disease data identifies a disease outbreak at one or more locations, and a time period for the disease outbreak. The disease movement monitor 140 is operable to determine one or more virtual zones 110 corresponding to the one or more locations of the disease outbreak. The disease movement monitor 140 is operable to determine whether any of the tracking devices 114 were located in the one or more virtual zones 110 within the time period using the timestamps and location information of the processed raw data sets. The disease movement monitor 140 is operable to update the disease movement data using the disease data and data for any tracking devices 114 that were determined to be located in the one or more virtual zones within the time period.

The alert generator 142, at 208, may generate an alert regarding any tracking devices 114 that were determined to be located in the one or more virtual zones 110 within the time period. The alert may provide transmitted to the relevant tracking devices 114, to the associated user device 122, or other user device 122, for example. The alert generator 142 may receive alert parameters to configure types of alerts, frequency of alerts, and so on for particular users of system 100.

The disease outbreak may also relate to one or more vectors or fomites (which in turn correspond to tracking devices) and the disease movement monitor 140 is operable to determine one or more virtual zones 110 that the corresponding tracking device 114 has visited during the relevant time period. The alert generator 142, at 208, may generate an alert relating to one or more virtual zones 110 that the corresponding tracking device 114 has visited during the relevant time period. The alert may be transmitted to the relevant user devices 122 associated with virtual zones 110 that the corresponding tracking device 114 has visited during the relevant time period, or other user device 122, for example.

At 210, a report generator 134 is operable for generating a report using the disease movement data. A user interface module 136 is operable to generate a variety of user interfaces for configuring a display of user device 112, tracking device 114, administrator device 124, and the like. The user interface may include report related information.

The reports may be generated for a variety of users (e.g. users associated with tracking devices 114, property owners, farmers, companies, vets, public health officials) and provided via user devices 122. The reports may be generated per user, per tracking device 114, per virtual zone 110, per disease, per geographic location (including multiple zones 110), per vector type, per fomite type, per company, and so on. The report may be transmitted to user device 122 for display as part of a user interface. The report may be a summary of disease records to allow users to pull up facts regarding disease (incubation, transmission mode). The reports may be a listing of recent outbreaks within a defined geographic area.

Local server 118 or central server 112 may receive report parameters from user device 112 (e.g. identifiers for user, tracking device 114, virtual zone 110, disease, geographic location (including multiple zones 110), vector type, fomite type, company, report type, time period, date range) at interface module 138 or report generator 134. Interface module 138 is operable to interact with report generator 134 to generate a report and provide the report to user device 122 as part of a user interface. A user interface may provide report as a chart, table, graph, map, and so on. The interface module 138 may generate web based interfaces, files for specific applications residing on user device 122, etc. The file preference may be received as a report parameter. The interface module 138 may also provide reports to administrator device 124. The reports may use data filtered based on access permissions. For example, a user may only have access to a limited amount of data, e.g. data for their tracking devices 114 or zones 110, while other users (e.g. administrators) may have a broader scope of access.

Figure 8:
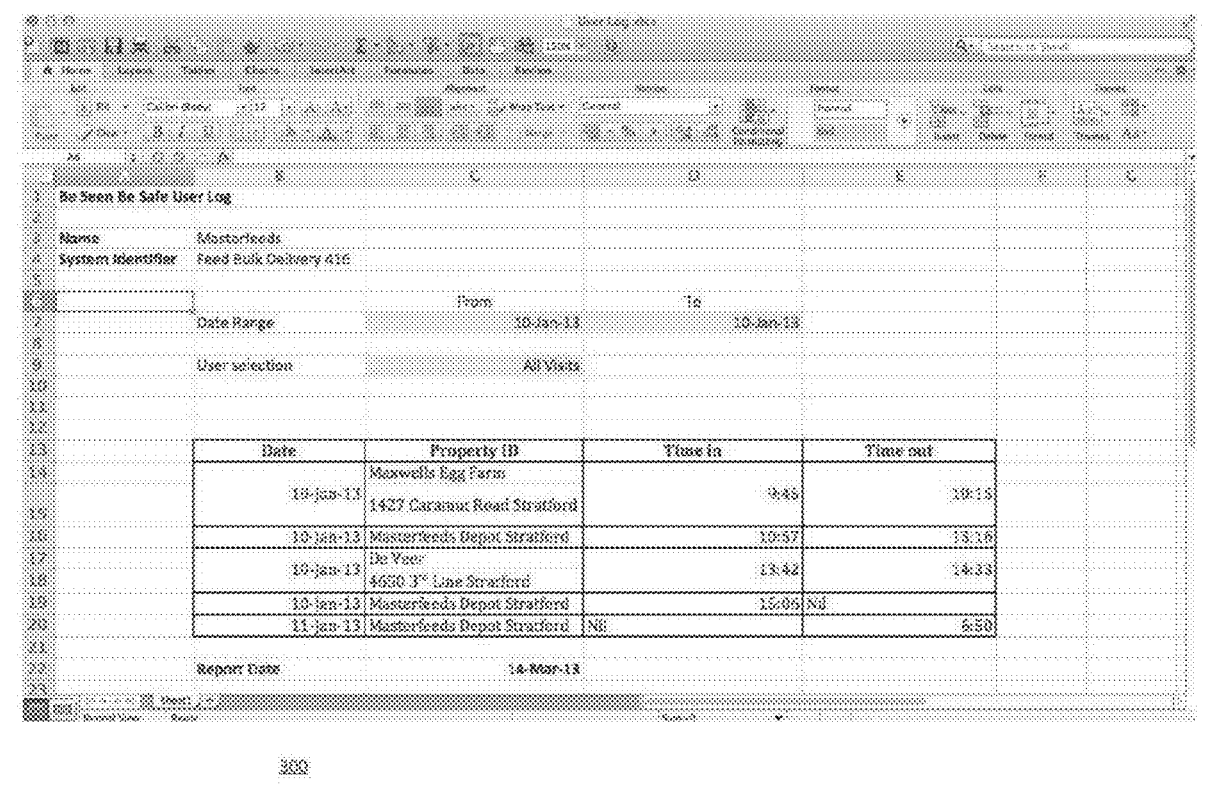

Referring now to FIG. 8, there is shown a schematic diagram of a user interface 300 providing a report for a user according to some embodiments.

An example type of user may be a user associated with a tracking device 114, for example (e.g. livestock owner, feed truck operator, delivery truck operator, supply truck operator), and may be able to track the movements of the tracking device 114 for a defined time period using a report or user interface. For example, the report or user interface 300 may be a spreadsheet or user log showing all visits to all zones 110 (e.g. movement) over a 12 month period. The report data may include the name of the user, a user identifier, the date range, and a type of visitor filter parameter (in this example "all visitors"). The report may include a log or table with a date of visit, a property identifier or name (for the zone 110 visited), time of entry, time of exit and so on. The report may also include a report date.

Figure 9:
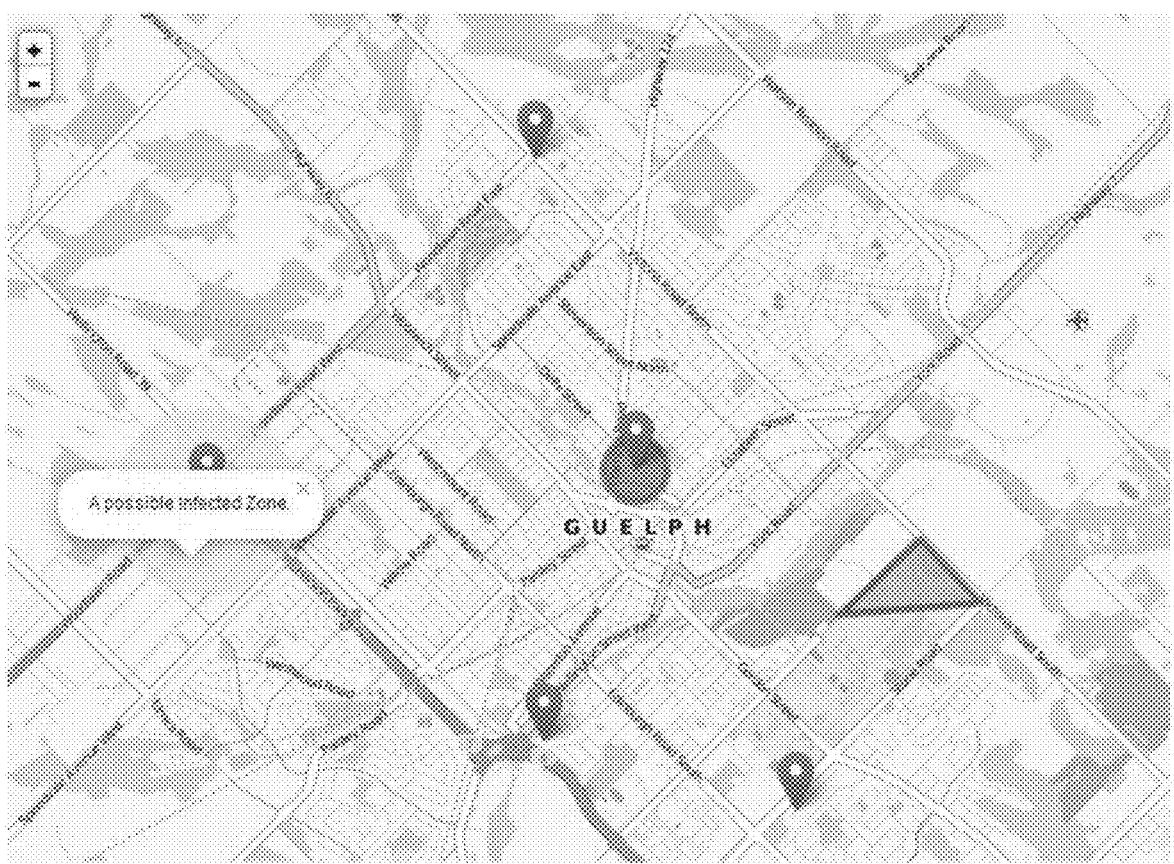
FIG. 9 is a schematic diagram of a user interface providing a mapping report according to some embodiments.

Referring now to FIG. 9, there is shown a schematic diagram of a user interface 320 providing a mapping report according to some embodiments. The mapping report may provide a map representing visits to all zones 110 (e.g. movement) over a time period. The zones 110 may be converted to longitude/latitude points with a property identifier or name (for the zone 110 visited). The map may also include disease related information such as a disease outbreak at a zone 110, a possibly infected zone 110, and so on.

Referring now to FIG. 10, there is shown a schematic diagram of a user interface 330 providing a report for a user according to some embodiments. Another example type of user is a property owner or manager. For example, the report or user interface 300 may be a spreadsheet or dynamic log showing all visits to one or more zone 110 of interest (e.g. the property or properties owned or managed by the user) over a 12 month period. The report data may include the name of the user, the date range, and a type of visitor filter parameter (in this example "all visitors"). The report may include a log or table with a date of visit, a visitor identifier or name (e.g. corresponding to the tracking device 114 that visited the property), time of entry, time of exit and so on. The report may also include a report date.

Figure 11:
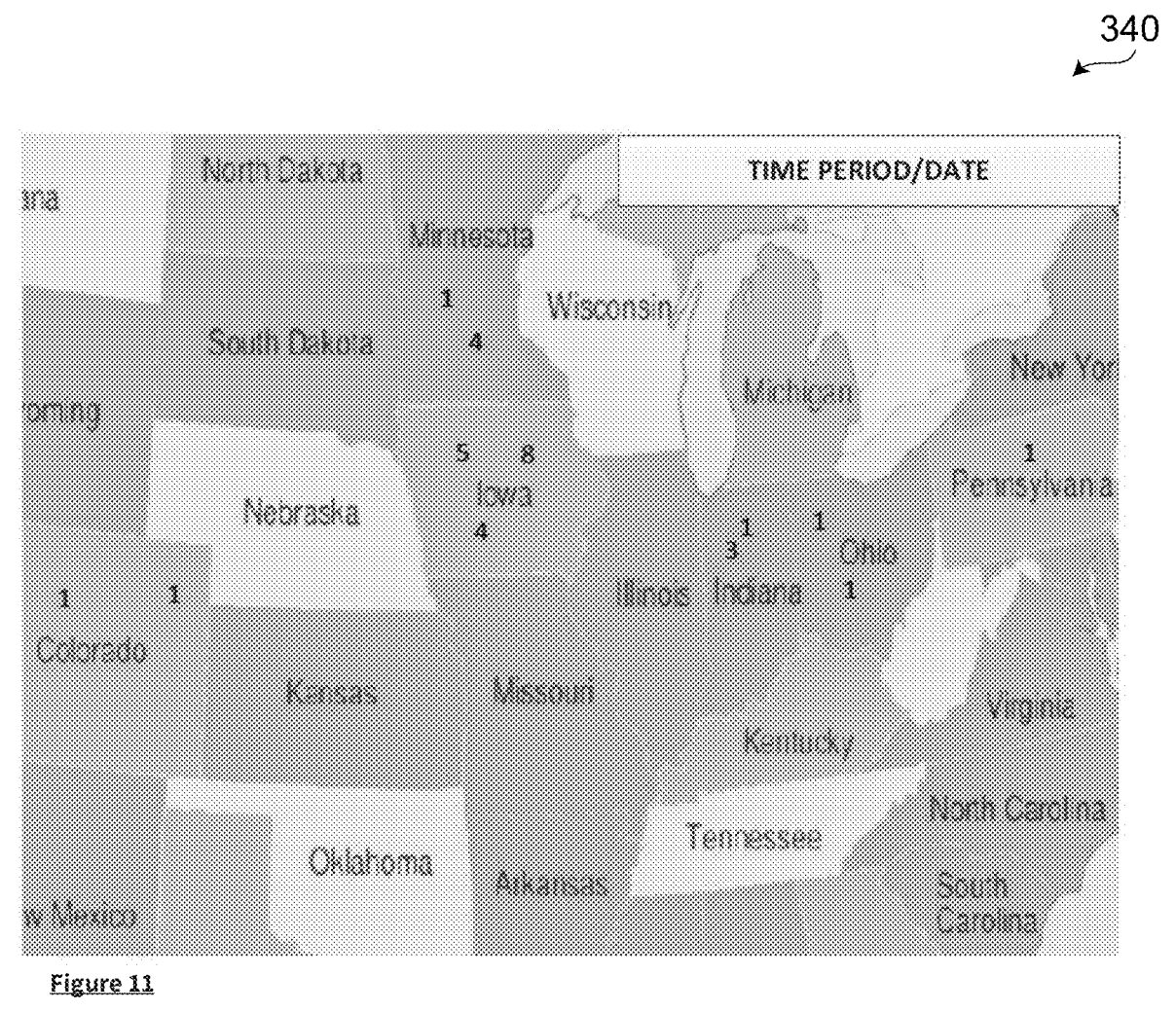

Referring now to FIG. 11, there is shown a schematic diagram of a user interface 340 providing another mapping report according to some embodiments. A user may be a public health official for example and may generate a report during a state of emergency (e.g. a disease outbreak). The user interface 340 may provide a map covering a large geographic area that aggregates data tracked by system 100.

The tracking may start from a suspect property and may fan out across all potentially infected properties where there is a connection back to the originally infected property. There may be varying degrees of connections from strong to remote. The user interface 340 may be a complex map showing a network of movement (along with an accompanying spreadsheet of movement data). The map may indicate disease outbreaks at certain locations and the number of reported infections, for example.

The report data may be displayed at many levels, such as national level showing a number of events across a country by province/county/state, a provincial/territorial/state level showing locations or zones 110 of potentially affected properties, a local level showing actual properties or zones 110, and so on. The map may be a heat map showing levels of risk assigned to each zone, or aggregated and averages by province/county/state.

The example map in the user interface 340 of FIG. 11 shows a national level report for a specified time period (e.g. report parameter).

Figure 12:
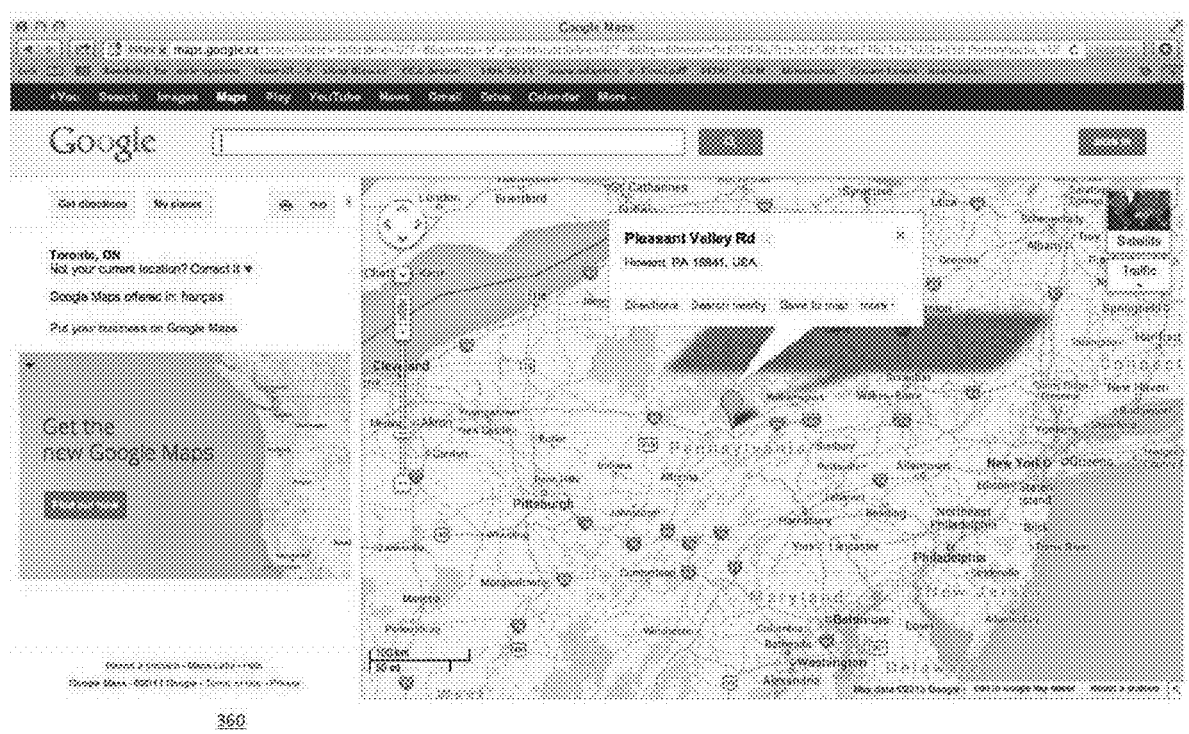
FIG. 12 is a schematic diagram of a user interface providing a further mapping report according to some embodiments.

Referring now to FIG. 12, there is shown a schematic diagram of a user interface 360 providing a further mapping report according to some embodiments. The example map shows a province/county/state level report. The map shows a zone 110 with a reported disease outbreak during a time period of interest (e.g. report parameter).

Figure 13:
FIG. 13 is a schematic diagram of a user interface providing another mapping report according to some embodiments.

Referring now to FIG. 13, there is shown a schematic diagram of a user interface 380 providing another mapping report according to some embodiments. The example map shows a local level report, including satellite images of a zone 110 (and coordinates) with a reported disease outbreak during a time period of interest (e.g. report parameter).

Central server 112 is configured to provide backtracking to disease origin or forward tracking to potential next outbreak and provide warnings/alerts that are general or targeted to business managers in the region. The triggers from tracking devices 114 may be activated through local transceiver devices 120 (e.g. cellular network, wireless hot spots, or through GPS), local servers 118, and so on.

The network connections of system 100 may secure via HTTPS for example. Data collectors 130 are operable to implement privacy restrictions on data by parsing private from non-private data prior to transmission. Accordingly, some servers 112, 118 may contain limited personal data, for example, if they are located outside of a jurisdiction as per user privacy preferences or regulatory restrictions. For example, certain local server 118 may not have information for properties outside of its jurisdiction.

When a user device 122 connects to central server 112 it may be automatically identified prior to receiving relevant information, such as a report. For example, central server may retrieve and match the MAC ID (e.g. unique identifier for the user) of the user device 122 with the user's information (e.g. user account record) to identify and authenticate users.

As system 100 records activities and events, if there is an outbreak, system 100 can isolate the specific location (e.g. one or more zones 110) and then trace back the source of the disease outbreak. System 100 may be proactive in terms of alerting first respondents based on location proximity and control the potential spread of the disease by being proactive in terms of the dissemination of information to the right individuals. By doing this, system 100 may help manage the costs and expediency of the disease control process.

System 100 is operable to deliver warnings or alerts (via alert generator 142) of a more general nature to all users (e.g. individuals or businesses) that are known from the data records on the server 112/118 to regularly travel in or through a region or zone 110 on a regular basis, that has recently been designated as a Primary Control Zone. Accordingly, zone 110 records may indicate a currently designated zone type, and may also store historical data of past types.

System 100 is also operable to dynamically generate zones 110 (via zone generator 132) in response to receiving data relating to a disease outbreak (e.g. in relation to a property or a vector/fomite) or suspect disease outbreak. For example, zone generator 132 is operable to create temporary geo-fences around hot properties and Primary Control Zones that will automatically generate warnings to tracking devices 114 entering the infectious zone.

When a tracking device 114 crosses a geofence zone 110, then the tracking device 114 triggers an event (push notification, opening doors, diming lights). These messaging activities (or alerts) may be called "Location Based Messaging" and may differ from the standard push "broadcast" messaging which is to message all users of the system regardless of their current location. Alert generator 142 may offer both types of messages, and additional alerts.

The tracking application 160 may be operable to implement the a variety of functionality, such as, for example: approximate location (network based) and precision location (GPS and network-based), automatically find accounts on the phone, provide full network access, control vibration, and may prevent device 114 from sleeping to track movement.

System 100 is also operable to trigger a multitude of other biosecurity and food safety responses such as using specific alerts and via an access controller coupled to access control infrastructure of a zone 110 (e.g. restricting entry, automatically locking or opening gates with pre-programmed entry protocols, efficiently and effectively broadcast regular status updates/bulletins to predetermined populations of interest, vets, service personnel and others who travel on and between zone on a regular basis).

Since system 100 records activities and events, if there is an outbreak, system 100 can isolate the specific location and then by using User Access Identity Profiles automatically figure out who has access to these "hot" areas or zones 110. An access controller coupled to access control infrastructure can block access to a zone 110 (e.g. doors can be automatically locked or unlocked depending on credentials, if user belongs to a lower-tier access profile the doors/gates will remain locked). System 100 is proactive in terms of alerting first respondents based on location proximity and effectively disseminate information via alerts and reports to the right individuals. By doing this, system 100 helps manage the costs and expediency of the disease control process.

Accordingly, system 100 may further include an access controller (e.g. at local server 118, central server 112) coupled to access infrastructure (e.g. gates, doors) for virtual zone(s) 110. The disease movement monitor 140 is further configured for receiving disease data that identifies a disease outbreak at one or more locations, and a time period for the disease outbreak. The disease movement monitor 140 may determine that a virtual zone 110 with the access infrastructure corresponds to one or more locations of the disease outbreak. The disease movement monitor 140 (e.g. in local server 118 or central server 112) may determine that a tracking device 114 is approaching the virtual zone 110 with the access infrastructure coupled to the access controller. The access controller may control the access infrastructure to deny entry into the virtual zone 110 of the vector or fomite corresponding to the approaching tracking device 114.

System 100 is also operable to allow veterinarians and public health workers (e.g. users) to easily record disease information in real time, which information may be uploaded and recorded to automatically update central server 112. This may trigger new zone 110 generation by zone generator 132, alerts by alert generator 142, updates to user records by user module 136, and updates to device 114 records by tracking module 144. Disease movement monitor 140 will process data to show the geographic movement/progress of a disease outbreak in real-time.

For example, a veterinarian may access central server 112 or local server 118 via user device 122 to receive reports of patterns for disease movement. The veterinarian can select from a drop down list of diseases on a user interface (generated by interface module 138) and once the veterinarian submits the form, the information will be stored at central server 112 or local server 118. No personal information about the farm, person owning/operating the farm may be stored or provided in a report, other than general location of the property. The data may then be aggregated by central server 112 or local server 118 into a geospatial map representing where potential hot spots are and the movement of diseases. This may trigger dynamic generation of zones 110, record updates, alerts, and so on.

Figure 3:
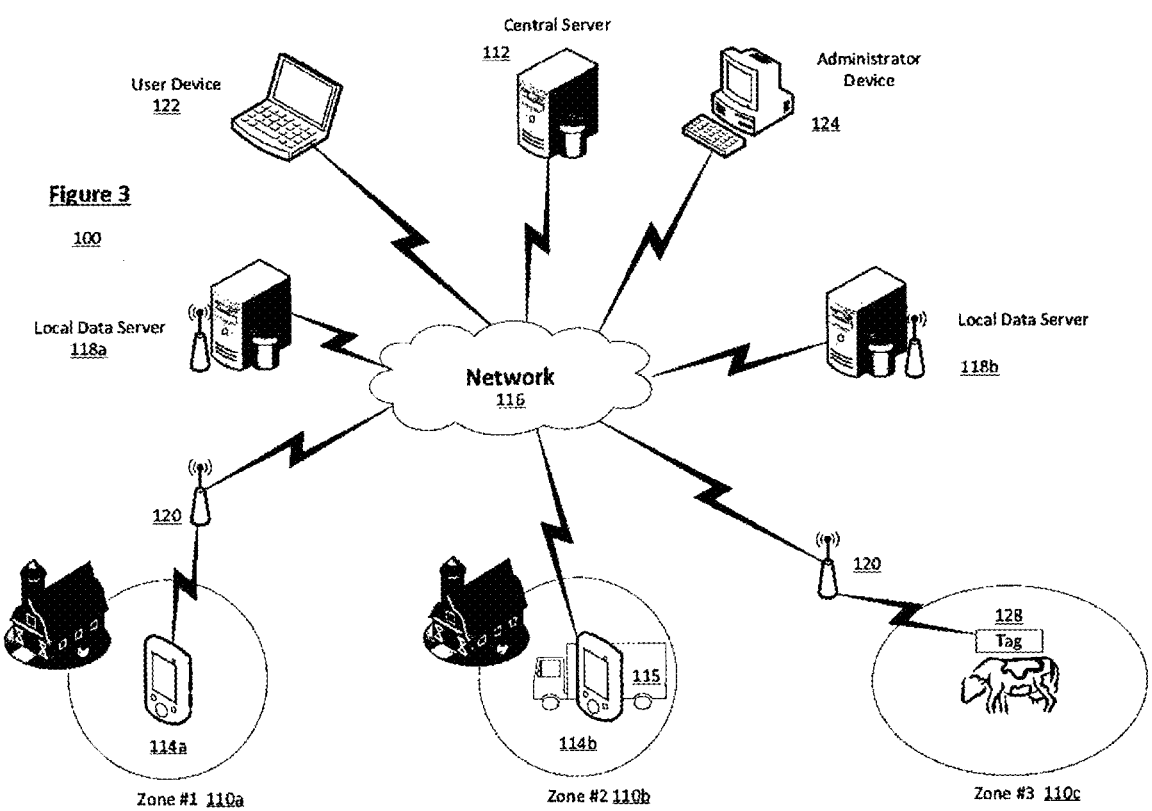
FIG. 3 is a schematic diagram of another system for monitoring movement of disease according to some embodiments.

Referring now to FIG. 3 there is shown another example schematic of a monitoring system 100 according to some embodiments. System 100 may track and trace movement of livestock via tags 128 which may be an illustrative example of a tracking device 114. System 100 may link raw data to electronic records and manifests for livestock (as received from system by user devices 122 for example).

System 100 is operable to track livestock movement using a tag 128 applied to individual livestock, using tracking devices 114 on trucks 115 for batches of livestock, and so on. This may compliment the general manifest of livestock that trucks have, which manifest may be recorded as part of a tracking device 114/128 record. System 100 is operable to record their activities in terms of movement by collecting location based information and processing it by matching it to zones 110. In addition, system 100 is operable to broadcast specific messages to a targeted audience (e.g. drivers) regarding livestock, disease, zones 110, etc. Furthermore, location based messaging may also be used. For example, if a truck is carrying only swine and there has been a swine outbreak, system 100 may prevent them from crossing boundaries of zones 110 with outbreak by closing gates automatically and sending their device 114 a message about why they are not permitted.

Figure 7:
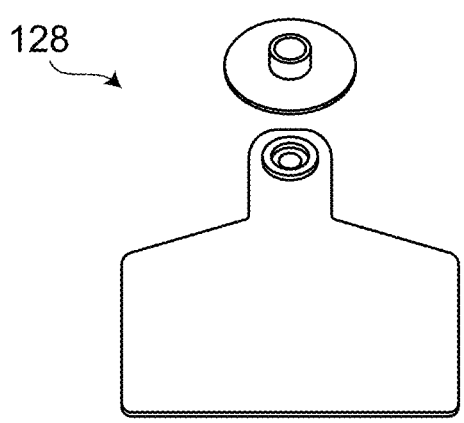
FIG. 7 is a schematic diagram of a tag (e.g. tracking device) for livestock according to some embodiments.

FIG. 7 illustrates a schematic diagram of a tag 128 (e.g. tracking device 114) for livestock according to some embodiments. This tag 128 may be used in the example system 100 shown in FIG. 3.

A tag 128 may be attached to the objects (e.g. vector, fomite) to be tracked. Two-way radio transceiver device 120 may send a signal to the tag and read its response.

The tags 128 may be battery assisted with an on-board battery. The tag 128 may periodically transmits its ID signal and location information to transceiver device 120. Tags 128 may be read/write, where object-specific data can be written into the tag by the system 100. The tag's information may be stored electronically in a non-volatile memory. The tag 128 may include a small transmitter and receiver, and a GPS device. The tags 128 may include an integrated circuit for storing and processing information, modulating and demodulating a signals, collecting power, and other specialized functions. The tags 128 may also include an antenna for receiving and transmitting signals.

The tag 128 may be a GPS device in combination an on-board battery. The tag 128 may be placed on the ear of livestock for example. The tag 128 may not require an external reader and the tag 128 may remotely and constantly read via the GPS device which would give the tag constant geo-location data which the system 100 could track. The tag may be a GPS device placed in a disk of an tag 128 for example. The battery may be a new flexible battery with a small size such as that created by Blue Spark Technologies as a non-limiting example. The battery may be placed in the tag portion of the eartag 128. The battery would power the miniature GPS chip that is capable of transmitting a signal that can be captured and used to track the livestock to which it is attached. A GPS microchip device and GPS antenna is created by Fastrax as a non-limiting example.

System 100 may be used for livestock surveillance where triggers can be made via zones 110 (e.g. wireless hotspots, Bluetooth, GPS). The servers 118 can convert GPS information into tag 128 specific data for storage as records. A farmer, producer, stock owner, etc. can manage livestock remotely via user device 122. System 100 may record livestock performance, remote tracking, prevent theft, track consignments for food safety, etc. An administrative user 124 can administer specific messages to drivers or groups of drivers, view their current location, and much more.

In some embodiments, central servers 112 may receive data feeds 126 (FIG. 2) from a variety of sources. The data feeds 126 may be correlated by date, time, location, etc. to disease and movement data captured by central server 112.

Data collector 130 may be further configured for receiving and preprocessing real-time data feeds 126. The data feeds may be normalized, reformatted, etc. to complement formatting and data structures of central server 112. The data feeds 126 may identify one or more locations, time periods, etc.

The disease movement monitor 140 may be further configured for determining virtual zones 110 that correspond to the location(s). The disease movement monitor 140 may determine disease related data from the data feeds 126 and the one or more virtual zones 110, and update the disease movement data using the determined disease data.

System 100 integrates and exploit a variety of forms of real-time data streams 126 to enhance understanding of seemingly unrelated events and integrate the data to form a new view of an event. For example, system 100 may integrate social media postings, with meteorological data and weather patterns, travel routes of possible vectors and fomites of disease (vets, feed company vehicles etc) and then aggregate the information together to form a highly weaved and rich meta-data view of an outbreak or any event. System 100 integrates not just clear disease events (disease spotted on farm) with less-relevant suspects (a feed company source of supply has been contaminated) which may lead to connections within large seemingly unconnected datasets. System 100 integrates other data streams in real time to get a holistic view. Central server 112 creates a rich dataset involving different types of data covering different aspects of disease.

System 100 has the capacity to report and analyze vector and fomite visits to and from hot properties and regions of interest for short or long time periods depending on when data was first collected. System 100 stores historical data for devices 114 and zones 110. The longer time periods may be longer than an incubation period for the diseases of interest to plant and animal agriculture.

The vector/fomite and disease collected raw data may be used to track backwards movements of other disease vectors and/or fomites that have visited the hot property to find out where they came from immediately before visiting the hot property. This enables the at risk properties visited prior to the outbreak on the hot property to be tested for the disease. The vector/fomite collected raw data may be used to track forwards movements of other disease vectors and/or fomites that have visited the hot property to find out which at risk properties they visited immediately following their visit to the hot property. This enables 'at risk' properties to be tested for the disease even before clinical signs have been observed.

The system 100 may create an accurate prioritized analysis of the potential disease movements before and after a hot property was confirmed infected. With this information those managing the disease outbreak, the Incident Commander, Regulators and Emergency Management Teams can take preventative action to stop the disease moving beyond those properties. It is important to attempt to prevent disease spread as soon as possible to prevent its uncontrolled spread.

A location-based tracking application 160 is programmed to react to a geotrigger event when the device 114, carried by a vector or fomite, crosses a geofence boundary. In order to activate tracking application 160 a user may be requested to enter the visitor information that is currently requested for the on farm food safety program such as name, company, occupation and contact details for use in the event of an emergency (e.g. registration data).

When entering the geofenced location (agricultural property) a text message (e.g. alert) provides a coded notification of the event that may be sent to a local server 118 or transceiver device 120. A tailored message may generated from the local server 118 related to the property which can be sent to the device 114 (i.e. reminder of biosecurity protocols or to call farmer for directions).

A central server 112 may draw a coded notification from the local server 118 into a database, where it is matched with the device 114 and geographical information on the geofenced property (e.g. zone 110) previously entered into the system 100.

In some embodiments, only one server performs required functions such as identification of property and/fomite, and tracking of movement of vectors/fomites between properties.

System 100 enables vectors/fomites to be tracked which represent potential "transporters of disease" and the zones 110 represent agricultural sites having livestock or crops on site.

System 100 provides the ability to track vectors and fomites with disease carrying potential entering and exiting agricultural facilities. Monitoring system 100 tracks the movement of a plurality of vectors and fomites across a plurality of agricultural facilities to provide a map-like output of locations most visited by vectors and fomites (e.g. reports). Real-time tracking allows for determination of locations previously visited by vectors and/or fomites prior to visiting an agricultural facility where a disease outbreak is identified. This would allow for relevant authorities to track locations of disease outbreak, spread of disease, and highest risk areas to appropriately assert protocols to mitigate disease spread.

In system 100, a geofence may define an agricultural location or zone 110. The tracking device 114 may be carried by a vector or fomite that has the potential to carry disease. Coded information may be received by a local server 118 and sent to a central server 112 to be decoded and processed to detect and generate information relevant for disease tracking. System 100 may enable tracking of vectors and fomites across a network of geofenced locations or zones 110, and interpret this data to provide information on at risk locations for disease outbreaks and spread. System 100 may provide the ability to provide warnings and alerts via electronic media to specific populations and users of interest. System 10 may create boundaries with appropriate alerts around Primary Control Zones (this currently requires a physical 'manned' presence). System 100 may provide the ability to link apparently unrelated data into a meta-analysis to look for causes.

System 100 may provide the ability for veterinarians and public health practitioners (e.g. users) to record and publish disease occurrence data in real time via user devices 122.

System 100 may be used for other applications. Examples include: Tracking consignments of livestock in transit for animal welfare monitoring; Synchronizing dispatch and arrival times for sensitive agricultural products (plant and animals); Monitoring vehicles carrying livestock across/between jurisdictions; Automating biosecurity entry protocols and systems for service personnel visiting farms in remote or unmanned locations; Automating biosecurity entry protocols and systems for disease management in multi-age livestock and poultry production systems; Tracking and tracing livestock and plants (batches) throughout production cycle through processing; Tracking of livestock in and out of geofenced areas; Controlling the movement of ranging livestock; Replacing conventional fences; Documenting of hours service providers spend at a specific location for billing purposes; Time-clock for employees; Tracking of zoonoses movement in human populations associated with agricultural premises; and the like.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various embodiments described herein.

The invention claimed is:

1. A system for monitoring disease across agricultural areas of interest, the system comprising:
   at least one processor; and
   a memory storing one or more sequences of instructions which, when executed by at least one processor, configures the at least one processor to:
   receive access notification information from at least one virtual zone corresponding to an agricultural geographic area of interest, wherein:
   the at least one virtual zone is defined by at least one geofence,
   each virtual zone is associated with a level of risk that indicates a likelihood of an outbreak of a disease detrimental to agriculture within the agricultural area of interest,
   each virtual zone is configured to receive access notification information from each geofence when tracked devices enter an area defined by that geofence, and
   the access information includes the level of risk associated with other virtual zones from which the tracked devices came; and
   transmit an alert message to a first device when the first device is in proximity to one of the at least one virtual zone, the alert message indicating if the first device should enter that virtual zone.

2. The system as claimed in claim 1, wherein the alert message is at least one of:
   based in part on a level of risk associated with that virtual zone;
   based in part on a level of risk associated with at least one other virtual zone from which the first device came; or
   associated with a profile associated with the first device, the alert message including quantitative information pertaining to the level of risk, the quantitative information including a protocol to be followed once registered devices having said profile enter the area.

3. The system as claimed in claim 1, wherein the at least one processor is configured to at least one of:
   transmit the alert message prior to the first device entering the virtual zone, the alert message indicating a warning to not enter the virtual zone; or
   transmit the alert message when the first device enters the virtual zone, the alert message indicating the level of risk associated with the virtual zone.

4. The system as claimed in claim 1, wherein the at least one processor is configured to at least one of:
   transmit the alert message prior to the first device entering the virtual zone, the alert message indicating that entry to the virtual zone is permitted; or
   transmit the alert message prior to the first device entering the virtual zone, the alert message indicating that entry to the virtual zone is restricted.

5. The system as claimed in claim 1, wherein the at least one processor is configured to:
   transmit a report of zones at which the first device has visited over a period of time, each visited zone corresponding to one of the at least one virtual zone, said report including at least one of:
      a property identifier for each visited zone;
      a date when the first device entered each visited zone;
      a time when the first device entered each visited zone;
      a date when the first device exited each visited zone; or
      a time when the first device exited each visited zone.

6. The system as claimed in claim 5, wherein the information pertaining to said visited zones further comprises a log of visited zones, wherein at least one of:
   the log of visited zones comprises virtual zones not identified as having a disease outbreak;
   the log of visited zones comprises at least one virtual zone assigned a level of risk indicating a likelihood of having a disease outbreak; or
   the log of visited zones comprises at least one virtual zone identified as having a disease outbreak.

7. The system as claimed in claim 1, wherein the at least one processor is configured to:
   transmit map information comprising at least one virtual zone corresponding to an agricultural geographic area of interest, the virtual zone defined by at least one geofence.

8. The system as claimed in claim 1, wherein the at least one processor is configured to:
   receive and process a plurality of raw data sets from a plurality of tracking devices tracking tracked devices, each tracked device corresponding to a vector or fomite that has the potential to carry a disease detrimental to agriculture, each raw data set corresponding to a tracked device and comprising an identification code identifying the tracked device, a timestamp corresponding to the time the raw data was generated by the tracking device that tracked the tracked device, and location information for the tracked device;
   generate disease movement data by correlating the raw data sets to the virtual zones to detect movement of the tracked devices within, between or across the virtual zones; and
   assign a level of risk to each vector or fomite, wherein the level of risk provides an indication of a likelihood of carrying the disease detrimental to agriculture, said level of risk to each vector or fomite becoming the level of risk of the tracked device associated with the vector or fomite.

9. The system of claim 8, wherein the at least one processor is configured to:
   transmit real-time data feeds, wherein the data feeds identify at least one of:
      one or more locations;
      a disease outbreak at one or more locations; or
      a time period;
   determine one or more virtual zones corresponding to the one or more locations;
   determine at least one of:
      disease data from the data feeds and the one or more virtual zones; or
      whether any of the tracked devices were located in the one or more virtual zones within the time period using the timestamps and location information of the raw data sets; and
   update the disease movement data using at least one of:
      the disease data; or
      data for any tracked devices that were determined to be located in the one or more virtual zones within the time period.

10. The system of claim 8, wherein the at least one processor is configured to:
    receive disease data, wherein the disease data identifies a disease outbreak at one or more locations, and a time period for the disease outbreak;
    determine that the virtual zone has access infrastructure and corresponds to the one or more locations with the disease outbreak;
    determine that a tracked device is approaching the virtual zone with the access infrastructure; and
    control access infrastructure to deny entry into the virtual zone of the vector or fomite corresponding to the approaching tracked device.

11. A method for monitoring disease across agricultural areas of interest, the method comprising:
    receiving access notification information from at least one virtual zone corresponding to an agricultural geographic area of interest, wherein:
       the at least one virtual zone defined by at least one geofence,
       each virtual zone associated with a level of risk that indicates a likelihood of an outbreak of a disease detrimental to agriculture within the agricultural area of interest,
       each virtual zone configured to receive access notification information from each geofence when tracked devices enter an area defined by that geofence,
       the access information including the level of risk associated with other virtual zones from which the tracked devices came; and
    transmitting an alert message to a first device when the first device is in proximity to one of the at least one virtual zone, the alert message indicating if the first device should enter that virtual zone.

12. The method as claimed in claim 11, wherein the alert message is at least one of:

based in part on a level of risk associated with that virtual zone;
based in part on a level of risk associated with at least one other virtual zone from which the first device came; or
associated with a profile associated with the registered device, the alert message including quantitative information pertaining to the level of risk, the quantitative information including a protocol to be followed once devices having said profile enter the area.

13. The method as claimed in claim 11, comprising at least one of:
transmitting, to the first device from a server, the alert message prior to the first device entering the virtual zone, the alert message indicating a warning to not enter the virtual zone; or
transmitting, to the first device from the server, the alert message when the first device enters the virtual zone, the alert message indicating the level of risk associated with the virtual zone.

14. The method as claimed in claim 11, comprising at least one of:
transmitting, to the first device from a server, the alert message prior to the first device entering the virtual zone, the alert message indicating that entry to the virtual zone is permitted; or
transmitting, to the first device from the server, the alert message prior to the first device entering the virtual zone, the alert message indicating that entry to the virtual zone is restricted.

15. The method as claimed in claim 11, comprising:
transmitting a report of zones at which the first device has visited over a period of time, each visited zone corresponding to one of the at least one virtual zone, said report including at least one of:
a property identifier for each visited zone;
a date when the first device entered each visited zone;
a time when the first device entered each visited zone;
a date when the first device exited each visited zone; or
a time when the first device exited each visited zone.

16. The method as claimed in claim 15, wherein the information pertaining to said visited zones further comprises a log of visited zones, wherein at least one of:
the log of visited zones comprises virtual zones not identified as having a disease outbreak;
the log of visited zones comprises at least one virtual zone assigned a level of risk indicating a likelihood of having a disease outbreak; or
the log of visited zones comprises at least one virtual zone identified as having a disease outbreak.

17. The method as claimed in claim 11, comprising:
transmitting, to the first device from the server, map information to be rendered at the first device, the map information comprising at least one virtual zone corresponding to an agricultural geographic area of interest, the virtual zone defined by at least one geofence.

18. The method as claimed in claim 11, comprising:
receiving a plurality of raw data sets from a plurality of tracking devices tracking tracked devices, each tracked device corresponding to a vector or fomite that has the potential to carry a disease detrimental to agriculture, each raw data set corresponding to a tracking device and comprising an identification code identifying the tracked device, a timestamp corresponding to the time the raw data was generated by the tracking device that tracked the tracked device, and location information for the tracked device; and
generating, at the server, disease movement data, by correlating the raw data sets to the virtual zones to detect movement of the tracked devices within, between or across the virtual zones; and
assigning a level of risk to each vector or fomite, wherein the level of risk provides an indication of a likelihood of carrying the disease detrimental to agriculture, said level of risk to each vector or fomite becoming the level of risk of the tracked device associated with the vector or fomite.

19. The method as claimed in claim 18, comprising:
transmitting real-time data feeds, wherein the data feeds identify at least one of:
one or more locations;
a disease outbreak at one or more locations; or
a time period;
determining one or more virtual zones corresponding to the one or more locations;
determining at least one of:
disease data from the data feeds and the one or more virtual zones; or
whether any of the tracked devices were located in the one or more virtual zones within the time period using the timestamps and location information of the raw data sets; and
updating the disease movement data using at least one of:
the disease data; or
data for any tracked devices that were determined to be located in the one or more virtual zones within the time period.

20. The method as claimed in claim 18, comprising:
receiving disease data, wherein the disease data identifies a disease outbreak at one or more locations, and a time period for the disease outbreak;
determining that the virtual zone has access infrastructure and corresponds to the one or more locations with the disease outbreak;
determining that a tracked device is approaching the virtual zone with the access infrastructure; and
controlling the access infrastructure to deny entry into the virtual zone of the vector or fomite corresponding to the approaching tracked device.

21. A non-transitory computer-readable medium storing one or more sequences of instructions which, when executed by at least one processor, configures the at least one processor to:
receive access notification information from at least one virtual zone corresponding to an agricultural geographic area of interest, wherein:
the at least one virtual zone is defined by at least one geofence,
each virtual zone is associated with a level of risk that indicates a likelihood of an outbreak of a disease detrimental to agriculture within the agricultural area of interest,
each virtual zone is configured to receive access notification information from each geofence when tracked devices enter an area defined by that geofence, and
the access information includes the level of risk associated with other virtual zones from which the tracked devices came; and
transmit an alert message to a first device when the first device is in proximity to a virtual zone, the alert message indicating if the first device should enter that virtual zone.

* * * * *

UNITED STATES PATENT AND TRADEMARK OFFICE
CERTIFICATE OF CORRECTION

| | |
|---|---|
| PATENT NO. | : 11,961,149 B2 |
| APPLICATION NO. | : 18/151700 |
| DATED | : April 16, 2024 |
| INVENTOR(S) | : Timothy Nelson and Joel Roberto Sotomayor |

It is certified that error appears in the above-identified patent and that said Letters Patent is hereby corrected as shown below:

On the Title Page

In Item (71):
"BE SEEN BE SAFE LTD., Guelph (CA)",
Should read as:
-- FARM HEALTH GUARDIAN LTD., Guelph (CA) --

Signed and Sealed this
Fourth Day of June, 2024

Katherine Kelly Vidal
*Director of the United States Patent and Trademark Office*